(12) United States Patent
Wang et al.

(10) Patent No.: US 12,740,698 B2
(45) Date of Patent: Sep. 22, 2026

(54) PREDICTING CLINICAL PARAMETERS RELATING TO GLAUCOMA FROM CENTRAL VISUAL FIELD PATTERNS

(71) Applicants: MASSACHUSETTS EYE AND EAR INFIRMARY, Boston, MA (US); THE SCHEPENS EYE RESEARCH INSTITUTE, INC., Boston, MA (US)

(72) Inventors: Mengyu Wang, Quincy, MA (US); Lucy Shen, Newton, MA (US); Tobias Elze, Boston, MA (US)

(73) Assignees: MASSACHUSETTS EYE AND EAR INFIRMARY, Boston, MA (US); THE SCHEPENS EYE RESEARCH INSTITUTE, INC., Boston, MA (US)

( * ) Notice: Subject to any disclaimer, the term of this patent is extended or adjusted under 35 U.S.C. 154(b) by 898 days.

(21) Appl. No.: 17/766,324

(22) PCT Filed: Oct. 2, 2020

(86) PCT No.: PCT/US2020/053946

§ 371 (c)(1),
(2) Date: Apr. 4, 2022

(87) PCT Pub. No.: WO2021/067699

PCT Pub. Date: Apr. 8, 2021

(65) Prior Publication Data

US 2024/0049960 A1 Feb. 15, 2024

Related U.S. Application Data

(60) Provisional application No. 62/909,386, filed on Oct. 2, 2019.

(51) Int. Cl.
*A61B 3/024* (2006.01)
*A61B 3/00* (2006.01)
(Continued)

(52) U.S. Cl.
CPC ............ *A61B 3/024* (2013.01); *A61B 3/0025* (2013.01); *G16H 10/60* (2018.01); *G16H 50/70* (2018.01)

(58) Field of Classification Search
CPC ....... A61B 3/0025; A61B 3/024; A61B 3/028; G16H 10/60; G16H 50/70
See application file for complete search history.

(56) References Cited

U.S. PATENT DOCUMENTS

2011/0190657 A1* 8/2011 Zhou .................... G16H 50/70 600/558
2017/0236282 A1 8/2017 Abramoff et al.
2018/0346981 A1 12/2018 Pierce et al.

OTHER PUBLICATIONS

Li F, Wang Z, Qu G, Song D, Yuan Y, Xu Y, Gao K, Luo G, Xiao Z, Lam DSC, Zhong H, Qiao Y, Zhang X. Automatic differentiation of Glaucoma visual field from non-glaucoma visual filed using deep convolutional neural network. BMC Med Imaging. Oct. 4, 2018;18(1):35. doi: 10.1186/s12880-018-0273-5. Erratum in: BMC Med Imaging. May 21, 2019;19(1):40. PMID: 30286740; PMCID: PMC6172715.

(Continued)

*Primary Examiner* — Brandi N Thomas
(74) *Attorney, Agent, or Firm* — Tarolli, Sundheim, Covell & Tummino LLP

(57) ABSTRACT

Systems and methods are provided for predicting clinical parameters relating to glaucoma from central visual field patterns. A system includes a processor, an output device, and a computer readable medium that stores executable instructions. The instructions provide a pattern decomposition component that receives a set of visual field data for a patient representing, for each of a plurality of locations in the central region of an eye of the patient, a deviation in sensitivity to a visual stimulus from an age-adjusted normal value and decomposes the set of visual field data into a linear (Continued)

combination of a set of patterns defined via archetypal analysis over a corpus of visual field data to provide a set of decomposition coefficients. A machine learning model determines a clinical parameter for the patient from at least the set of decomposition coefficients, and a user interface provides the determined clinical parameter to a user.

15 Claims, 9 Drawing Sheets

(51) Int. Cl.
*G16H 10/60* (2018.01)
*G16H 50/70* (2018.01)

(56) References Cited

OTHER PUBLICATIONS

Kim, Paul Y., et al. "Selective fusion of structural and functional data for improved glaucoma detection." Modeling and Artificial Intelligence in Ophthalmology 1.3 (2017): 82-99.

International Search Report for Corresponding Application Serial No. PCT/US2020/053946, Date Jan. 11, 2021.

Elze et al: "Patterns of functional vision loss in glaucoma determined with archetypal analysis," J. R. Soc. Interface 12: 20141118, 2014, http://dx.doi.org/10.1098/rsif.2014.1118.

De Moraes et al: "24-2 Visual Fields Miss Central Defects Shown on 10-2 Tests in Glaucoma Suspects, Ocular Hypertensives, and Early Glaucoma," Ophthalmology 124: 1449-56, 2017, doi:10.1016/j.ophtha.2017.04.021.

Carreras et al: "Modeling the Patterns of Visual Field Loss in Glaucoma," Optometry and Vision Science 88: E63-79, Jan. 2011, DOI: 10.1097/OPX.0b013e3181fc310b.

Atalay et al: "Pattern of Visual Field Loss in Primary Angle-Closure Glaucoma Across Different Severity Levels," Ophthalmology 2016, 1957-64, vol. 123, DOI:https://doi.org/10.1016/j.ophtha.2016.05.026, American Academy of Ophthalmology.

Verma et al: "Visual Field Progression in Patients with Primary Angle-Closure Glaucoma Using Pointwise Linear Regression Analysis," Ophthalmology 2017, 1065-71, vol. 124, DOI:https://doi.org/10.1016/j.ophtha.2017.02.027, American Academy of Ophthalmology.

* cited by examiner

PREDICTING CLINICAL PARAMETERS RELATING TO GLAUCOMA FROM CENTRAL VISUAL FIELD PATTERNS

RELATED APPLICATIONS

The present application claims priority to U.S. Provisional Patent Application Ser. No. 62/909,386 filed Oct. 2, 2019 entitled PREDICTING CLINICAL PARAMETERS RELATING TO GLAUCOMA FROM CENTRAL VISUAL FIELD PATTERNS, the entire contents of which being incorporated herein by reference in its entirety for all purposes.

TECHNICAL FIELD

The present invention relates generally to the field of medical systems, and more particularly to predicting clinical parameters relating to glaucoma from central visual field patterns.

BACKGROUND

Glaucoma is a group of eye diseases which result in damage to the optic nerve and cause vision loss. The most common type is open-angle glaucoma with less common types including closed-angle glaucoma and normal-tension glaucoma. Open-angle glaucoma develops slowly over time and there is no pain. Peripheral vision may begin to decrease followed by central vision resulting in blindness if not treated. Vision loss from glaucoma, once it has occurred, is permanent. Glaucoma has been called the "silent thief of sight" because the loss of vision usually occurs slowly over a long period of time. Worldwide, glaucoma is the second-leading cause of blindness after cataracts.

SUMMARY

In accordance with an aspect of the present invention, a system includes a processor, an output device, and a non-transitory computer readable medium that stores instructions executable by the processor. When executed, the instructions provide a pattern decomposition component that receives a set of visual field data for a patient representing, for each of a plurality of locations in the central region of an eye of the patient, a deviation in sensitivity to a visual stimulus from an age-adjusted normal value and decomposes the set of visual field data into a linear combination of a set of patterns defined via archetypal analysis over a corpus of visual field data to provide a set of decomposition coefficients. A machine learning model determines a clinical parameter for the patient from at least the set of decomposition coefficients, and a user interface provides the determined clinical parameter to a user at the output device.

In accordance with another aspect of the present invention, a method is provided. A set of visual field data is obtained for a patient representing, for each of a plurality of locations in the central region of the eye, a deviation in sensitivity to a visual stimulus from an age-adjusted normal value. The set of visual field data is decomposed into a linear combination of a set of patterns defined via archetypal analysis over a corpus of visual field data to provide a set of decomposition coefficients. A clinical parameter is determined for the patient at a machine learning model from at least the set of decomposition coefficients. The determined clinical parameter is provided to a user at a display.

In accordance with yet another aspect of the present invention, a system includes a processor, an output device, and a non-transitory computer readable medium that stores instructions executable by the processor. When executed, the instructions provide a preclassifier that classifies the patient into one of a plurality of categories representing the severity of glaucoma for the patient and selects the set of patterns from a plurality of sets of patterns defined via archetypal analysis according to the category into which the patient is classified. A pattern decomposition component that receives a set of visual field data for a patient representing, for each of a plurality of locations in the central region of an eye of the patient, a deviation in sensitivity to a visual stimulus from an age-adjusted normal value and decomposes the set of visual field data into a linear combination of the selected set of patterns to provide a set of decomposition coefficients. A machine learning model determines a clinical parameter for the patient from at least the set of decomposition coefficients, and a user interface provides the determined clinical parameter to a user at the output device.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

The preservation of central visual function is essential to the care of glaucoma patients. Modeling central visual function as ascertained from 10-2 visual fields (VFs) with adequate sampling of the central 10 degrees offers an opportunity to categorize patterns of central vision loss in glaucoma and understand factors that contribute to its progression. By identifying standard patterns in central field vision loss, it is possible to predict the progression of glaucoma even at early stages of the disease. As a result, an informed selection of individuals for specific interventions and clinical trials can be made using readily obtained visual field data.

For the purpose of this application, a "deviation" is a measure of a variation of visual acuity for a patient from an age-adjusted standard at a given location, generally measured in decibels. A "mean deviation" is an arithmetic mean of the absolute deviation across all locations in a given visual field test. A "pattern standard deviation" is a measure of the average of the absolute difference between the deviation at each location of and the mean deviation.

Figure 1:
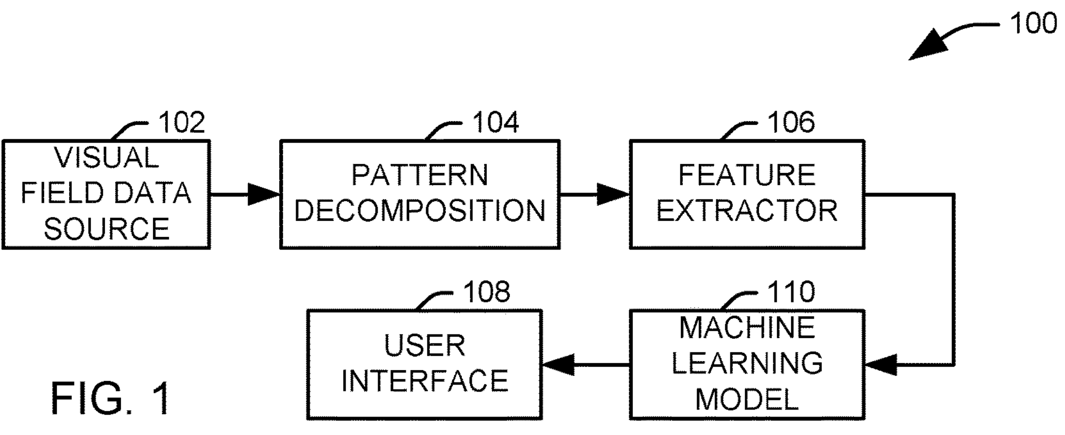
FIG. 1 illustrates a functional block diagram of an example of a system for predicting clinical parameters relating to glaucoma from central visual field patterns.

FIG. 1 illustrates a functional block diagram of an example of a system 100 for predicting clinical parameters relating to glaucoma from central visual field patterns. The system 100 can be implemented on one or more physical devices (e.g., servers) that may reside in a cloud computing environment or on a computer, such as a laptop computer, a desktop computer, a tablet computer, a workstation, or the like. In the present example, although the components 102, 104, 106, 108, and 110 of the system 100 are illustrated as being implemented on a same system, in other examples, the different components could be distributed across different systems and communicate, for example, over a network, including a wireless network, a wired network, or a combination thereof. The system 100 includes a visual field data source 102 that can be accessed to provide at least one visual field pattern to a pattern decomposition component 104. Since the system 100 utilizes central visual field patterns, the visual field data can be, for example, 10-2 visual field data. The visual field data source 102 can include, for example, any of a storage medium accessible by a local bus or a network connection, a visual field analyzer, or a user interface at which a user can enter information from a previous visual field scan.

Figure 2:
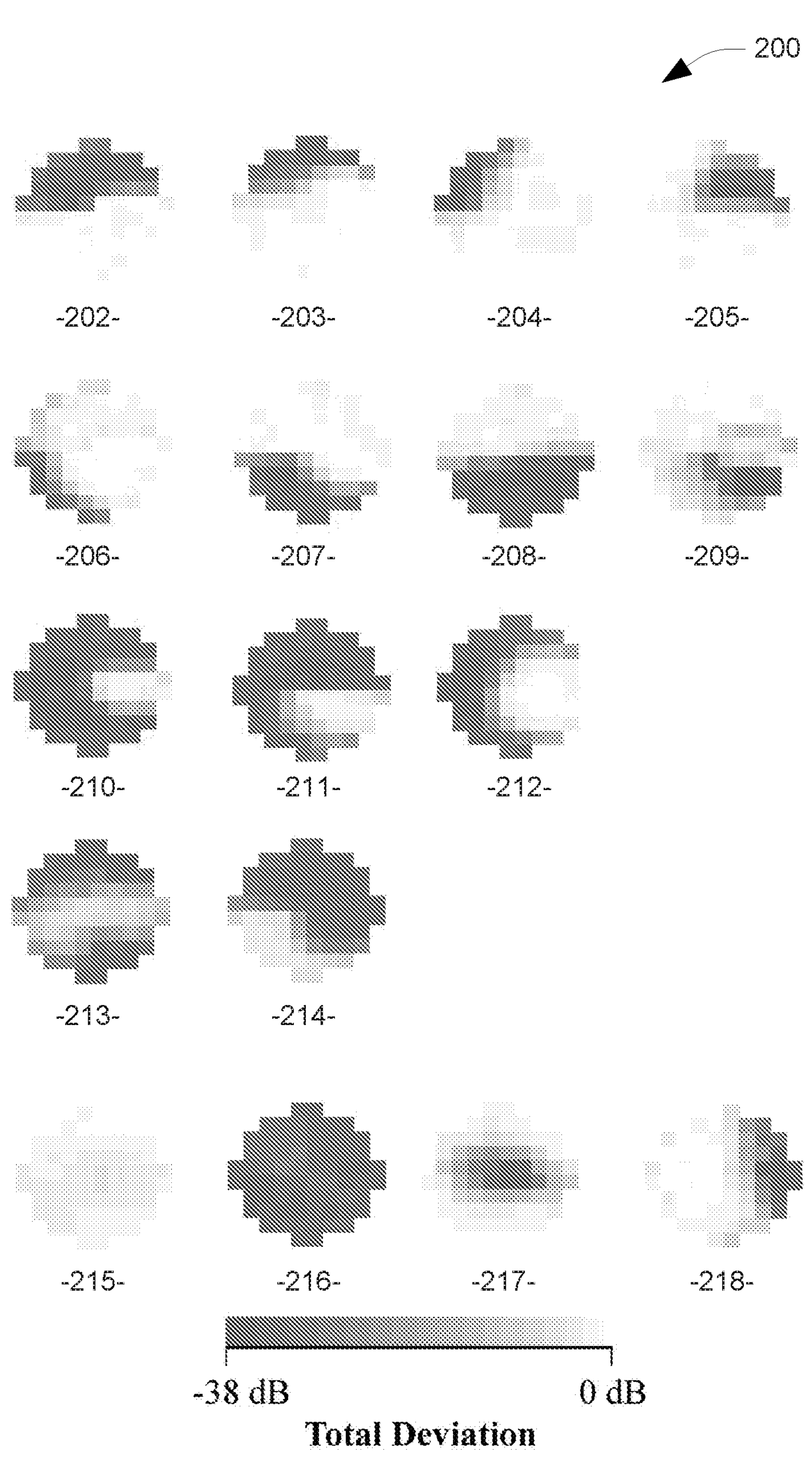
FIG. 2 illustrates an example of a set of archetypal visual field patterns.

A pattern decomposition component 104 is programmed to decompose a set of visual field data representing a patient into a linear combination of a defined set of visual field patterns. The defined set of visual field patterns can include a basis set of patterns defined via archetypal analysis over a corpus of visual field data. A new vector of visual field data can be decomposed into a linear combination of these basis vectors to provide a set of coefficients representing the visual field data. An example of a set of archetypal visual field patterns 200 is illustrated in FIG. 2. In the illustrated example, seventeen archetypal visual field patterns are illustrated. It will be appreciated that the archetypal patterns, since they are extracted via archetypal analysis, provide clinically recognizable and therefore are readily interpretable by a physician. Similarly, the coefficients extracted at the pattern decomposition component 104 can provide useful metrics for distinguishing among different presentations of glaucoma, and thus useful features for predicting the clinical parameter.

The archetypal patterns 202-218 can be divided into four general categories. A first set of patterns 202-205 represent loss of visual acuity in the superior portion of the visual field. Speaking generally, a first pattern 202 represents more general loss in the superior portion of the visual field, two patterns 203 and 204 represent loss in the nasal region of the superior portion of the visual field, and one pattern 205 represents loss in the temporal region of the superior portion of the visual field. A second set of patterns 206-209 represent loss of visual acuity in the inferior portion of the visual field. A first pattern 206 represents a loss in the periphery of the nasal region of the inferior portion of the visual field. A second pattern 207 represents a more general loss in the inferior region, weighted toward the nasal region, while a third pattern 208 represents a more balanced inferior loss. A fourth pattern 209 represents a pattern centered in the temporal region of the inferior portion of the visual field.

A third set of patterns 210-214 represent diffuse patterns of loss of visual acuity. Each of the first three patterns 210-212 represents a diffuse loss patterns with various regions of low loss on the temporal side of the visual field, which is, in general, less vulnerable to damage from glaucoma. A fourth pattern 213 represents loss in the superior and inferior peripheries, and a fifth pattern 214 represents a diffuse pattern across the superior region and the temporal portion of the inferior region. A fourth set of patterns 215-218 includes a first pattern 215 representing an intact field, a second pattern 216 representing loss across the entire field, a third pattern 217 representing the center of the visual field, and a fourth pattern 218 representing loss in the temporal region of the visual field.

A feature extractor 106 generates a feature vector that includes at least one of the set of coefficients generated at the pattern decomposition component 104. It will be appreciated that the feature extractor 106 can also utilize additional parameters, for example, general biometric parameters of the patient, such as blood pressure, blood glucose level, age, and sex, and properties of the eye, such as intraocular pressure and coefficients for Zernike polynomials. These parameters can be provided, for example, from an electronic health records database via a network interface (not shown) or via a user interface 108. Additional features can include global indices derived from one or more visual field patterns, including the average of mean deviation (MD) and pattern standard deviation (PSD) across one or more visual field patterns as well as a rate of change for MD and PSD between visual field patterns when multiple patterns are available. A mean absolute error (MAE) for one or more visual field patterns can be determined as the mean absolute difference between total deviation values at each of the locations in visual field pattern and a reconstructed baseline visual field generated as the sum of the archetypal patterns weighed by the set of coefficients.

A machine learning model 110 determines at least one clinical parameter for the patient from the metric. It will be appreciated that the clinical parameter can represent the presence or progression of glaucoma, a predicted or actual response to a clinical intervention, an intervention most likely to be successful, an expected or actual change in the visual acuity of a patient, or a likelihood representing any of the categorical parameters listed above. The clinical parameter provided by the machine learning model 110 can be stored on a non-transitory computer readable medium associated with the system and/or provided to a user at a display via the user interface 108.

Figure 3:
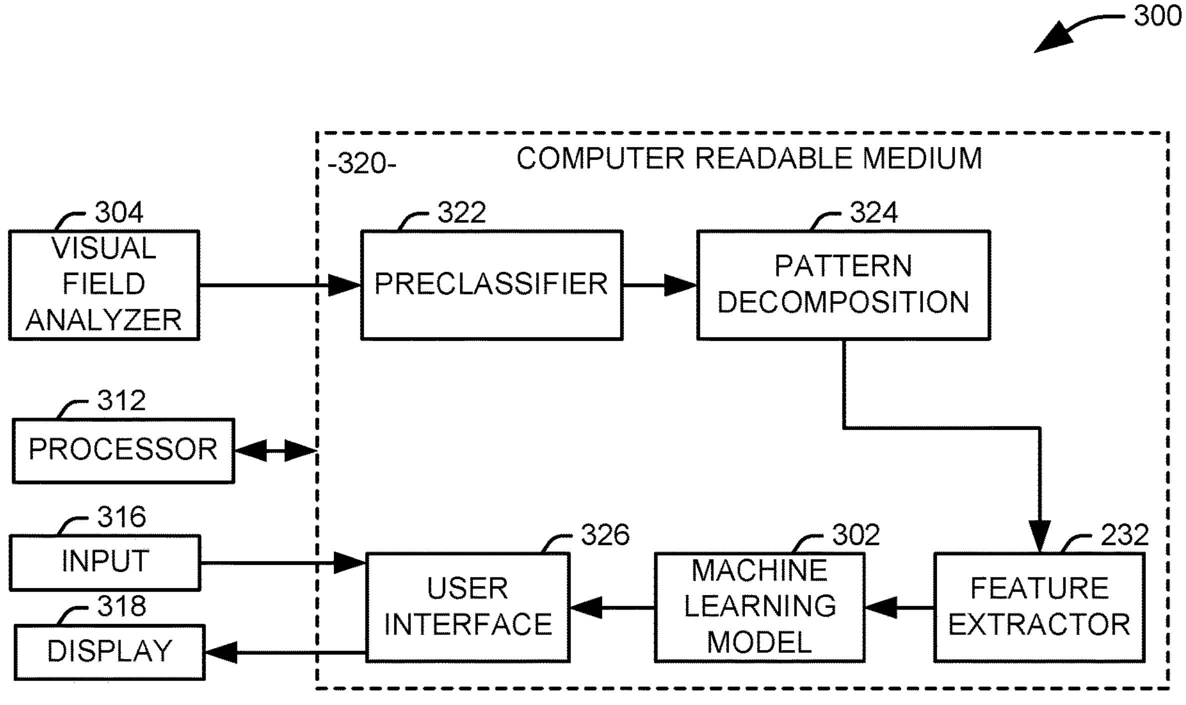
FIG. 3 illustrates a functional block diagram of an example of a system for predicting clinical parameters relating to glaucoma from central visual field patterns.

FIG. 3 illustrates a functional block diagram of an example of a system 300 for predicting clinical parameters relating to glaucoma from central visual field patterns. To this end, the system 300 incorporates a machine learning model 302 that utilizes features generated from a decomposition of visual field data into archetypal parameters to generate a categorical or continuous clinical parameter representing a diagnosis, a prognosis, or a response to treatment for the patient. In the illustrated implementation, a visual field analyzer 304 provides visual field data for a patient to a data analysis component implemented as a general-purpose processor 312 operatively connected to a non-transitory computer readable medium 320 storing machine executable instructions. In the illustrated system 300, the visual field data can include not only the 10-2 visual field data used to evaluate the central field, but also 24-2 visual field data that gives an indication of visual acuity for the entire eye. An input device 316, such as a mouse or a keyboard, is provided to allow a user to interact with the system, and a display 318 is provided to display visual field data and calculated parameters to the user.

In the illustrated implementation, the machine executable instructions include a preclassifier 322 that classifies a user into one of a plurality of categories representing different levels of severity or types of presentation of glaucoma. In the illustrated implementation, the preclassifier 322 classifies the patient into one a mild glaucoma category, a moderate glaucoma category, a severe glaucoma category, and an end-stage glaucoma category based on the 24-2 visual field data. The preclassifier 322 can utilize any appropriate classification model for this determination, although in the illustrated implementation, the patient's eyes are sorted according to a mean deviation across the eye. Eyes with mild glaucoma had a 24-2 visual field with a mean deviation greater than −6 dB, eyes with moderate glaucoma had a 24-2 visual field with a mean deviation between −12 dB and −6 dB, eyes with severe glaucoma had a 24-2 visual field with a mean deviation between −22 dB and −12 dB, and eyes with end-stage glaucoma having a mean deviation greater than −22 dB.

Figure 4:
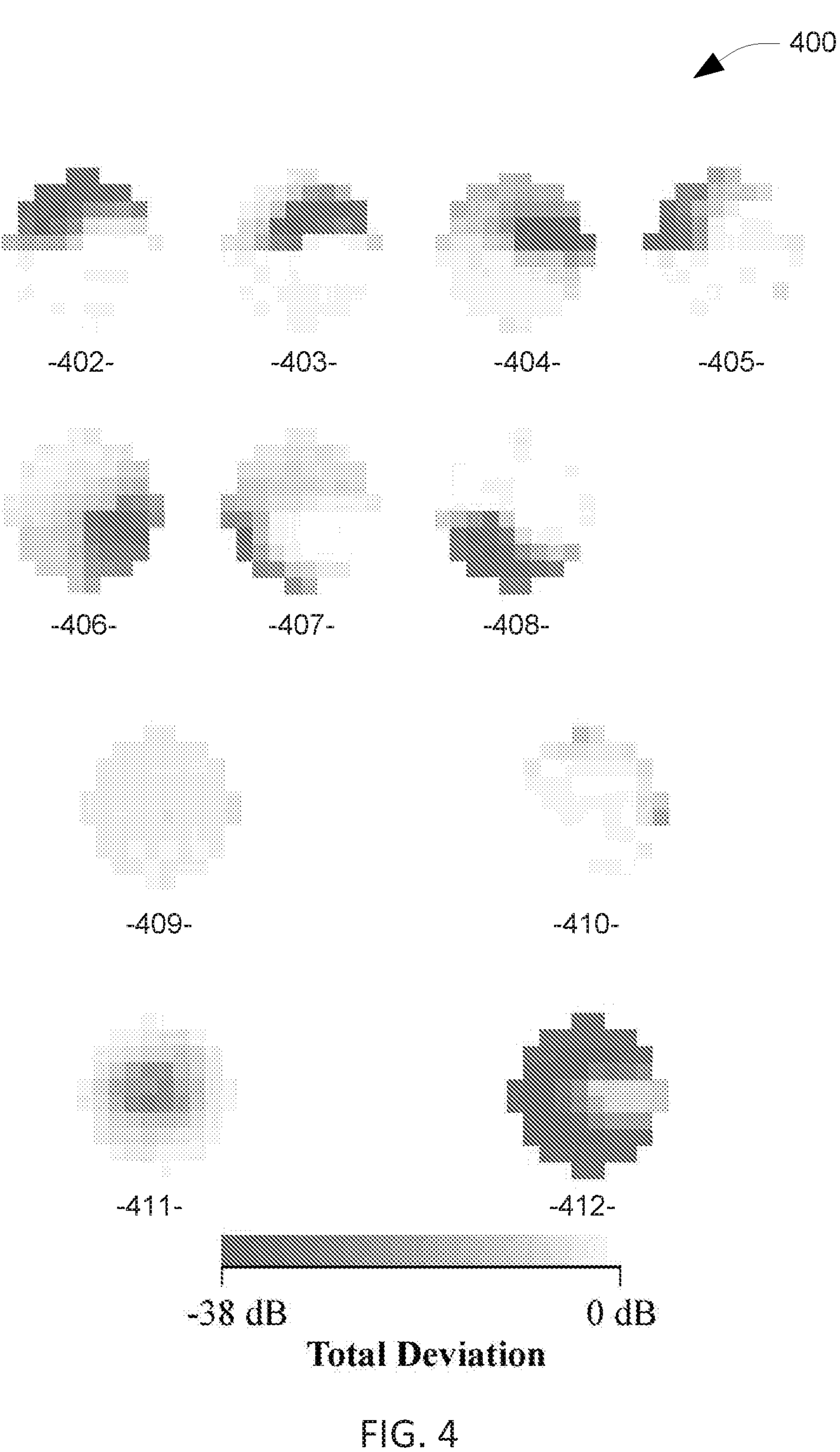
FIG. 4 illustrates an example of an archetypal basis set of visual field patterns that can be used at the pattern decomposition component for patients with mild glaucoma.
Figure 5:
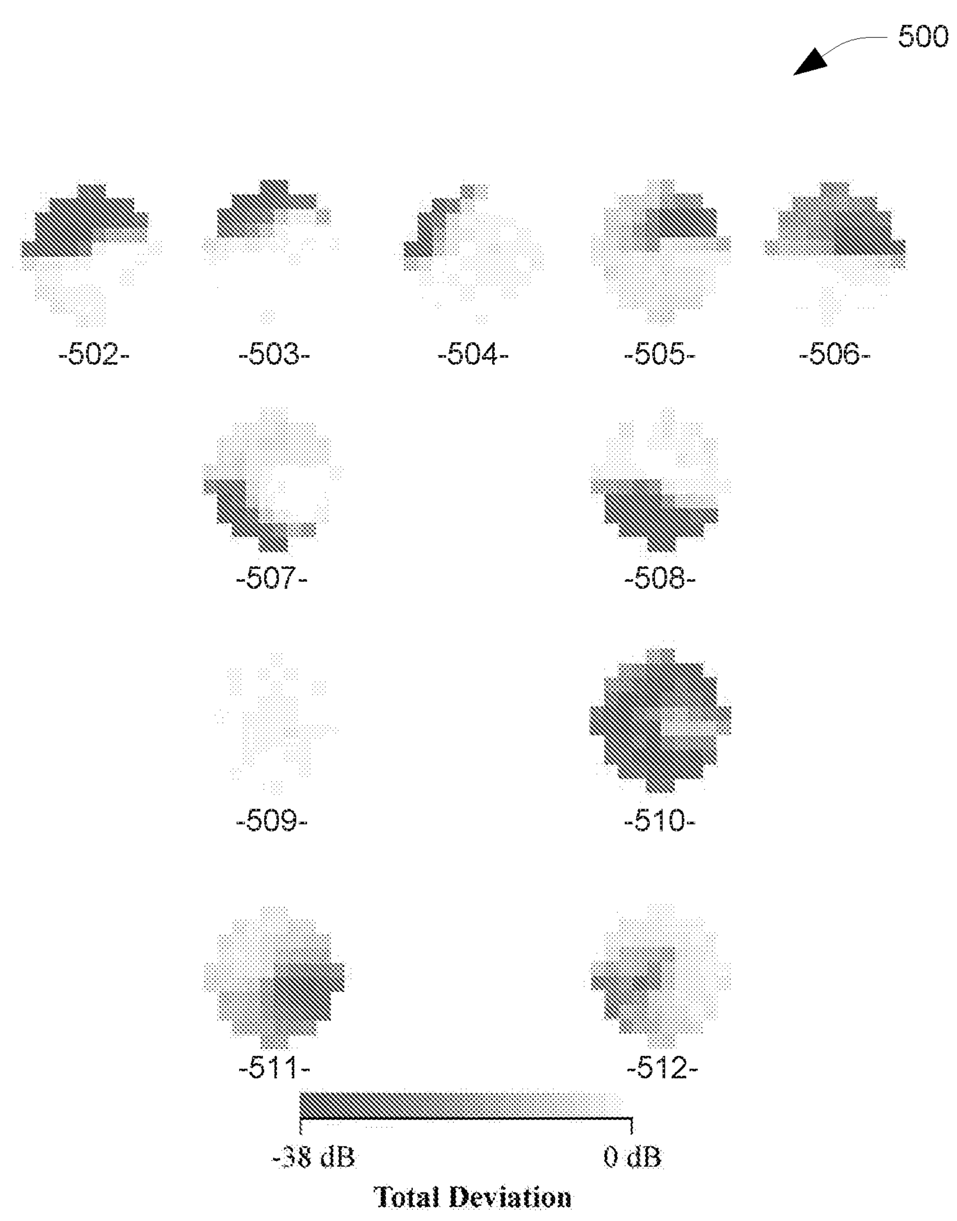
FIG. 5 illustrates an example of an archetypal basis set of visual field patterns that can be used at the pattern decomposition component for patients with moderate glaucoma.
Figure 6:
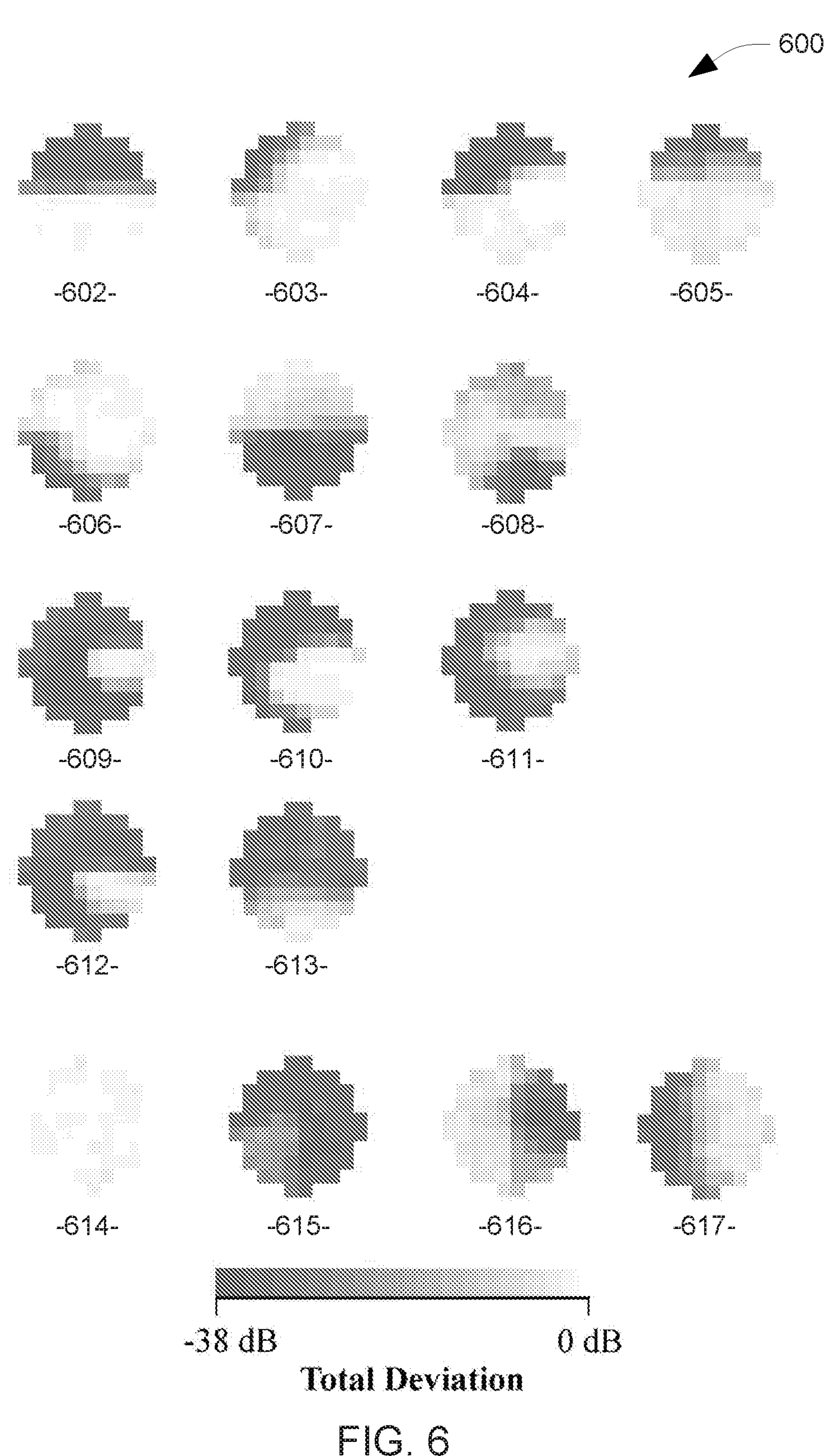
FIG. 6 illustrates an example of an archetypal basis set of visual field patterns that can be used at the pattern decomposition component for patients with severe glaucoma.

A pattern decomposition component 324 is programmed to decompose the 10-2 visual field data into a linear combination of a defined basis set of visual field patterns to generate a set of coefficients characterizing the visual field data. As in the system 100 of FIG. 1. The defined basis set is defined via archetypal analysis over a corpus of visual field data. In the illustrated example, however, multiple basis sets can be generated, each representing one of the plurality of categories associated with the preclassifier 322. The basis set used at the pattern decomposition component 324 for each patient can therefore be assigned according to the category assigned to that patient at the preclassifier 322. FIGS. 4-6 illustrate sets of archetypal visual field patterns for patients categorizes with mild glaucoma, moderate glaucoma, and severe glaucoma, respectively.

FIG. 4 illustrates an example of an archetypal basis set 400 of visual field patterns that can be used at the pattern decomposition component 324 for patients with mild glaucoma. The archetypal patterns 402-412 can be divided into three general categories. A first set of patterns 402-405 represent loss of visual acuity in the superior portion of the visual field. A first pattern 402 represents general loss in the superior portion of the visual field, weighted slightly toward the nasal side, a second pattern 403 represents general loss in the superior portion of the visual field, a third pattern 404 represents loss in the temporal region of the superior portion of the visual field, and a fourth pattern 405 represents loss in the periphery of the nasal region of the superior portion of the visual field.

A second set of patterns 406-408 represent loss of visual acuity in the inferior portion of the visual field. A first pattern 406 represents a more general loss in the inferior region, weighted toward the nasal region. A second pattern 407 represents a loss in the periphery of the nasal region of the inferior portion of the visual field. A third pattern 408 represents loss in the nasal region of the inferior portion of the visual field. A third set of patterns 409-412 represent patterns of loss of visual acuity that are present in the superior and the inferior regions. A first pattern 409 represents an intact field, a second pattern 410 representing loss in the periphery of the central visual field, and a third pattern 411 representing the center of the visual field. A fourth pattern 412 represents a diffuse loss pattern with a region of low loss in the center of the temporal side of the visual field.

FIG. 5 illustrates an example of an archetypal basis set 500 of visual field patterns that can be used at the pattern decomposition component 324 for patients with moderate glaucoma. The archetypal patterns 502-512 can be divided into three general categories. A first set of patterns 502-506 represent loss of visual acuity in the superior portion of the visual field. A first pattern 502 represents general loss in the superior portion of the visual field, weighted slightly toward the nasal side, and a second pattern 503 represents general loss in the superior portion of the visual field. A third pattern 504 represents loss in the periphery of the nasal region of the superior portion of the visual field. A fourth pattern 505 represents loss in the temporal region of the superior portion of the visual field, and a fifth pattern 506 represents general loss in the superior portion of the visual field, weighted slightly toward the nasal side.

A second pair of patterns 507 and 508 each represents loss of visual acuity in the inferior portion of the visual field. A first pattern 507 represents a loss in the periphery of the nasal region of the inferior portion of the visual field. A second pattern 508 represents loss in the nasal region of the inferior portion of the visual field. A third set of patterns 509-512 represent patterns of loss of visual acuity that are present in the superior and the inferior regions. A first pattern 509 represents an intact field, and a second pattern 510 represents a diffuse loss pattern with a region of low loss in the center of the temporal side of the visual field. A third pattern 511 represents loss on the temporal side of the field, weighted toward the inferior portion of the visual field, and a fourth pattern 512 represents loss of the nasal side.

FIG. 6 illustrates an example of an archetypal basis set 600 of visual field patterns that can be used at the pattern decomposition component 324 for patients with severe glaucoma. The archetypal patterns 602-617 can be divided into four general categories. A first set of patterns 602-605 represent loss of visual acuity in the superior portion of the visual field. Speaking generally, a first pattern 602 represents more general loss in the superior portion of the visual field, and a second pattern 603 represents loss in the periphery of the nasal side superior portion of the visual field. A third pattern 604 represents loss across the superior portion of the visual field, weighted toward the nasal side, and a fourth pattern 605 represents loss in the periphery of the superior portion of the visual field. A second set of patterns 606-608 represent loss of visual acuity in the inferior portion of the visual field. A first pattern 606 represents a loss in the periphery of the nasal region of the inferior portion of the visual field. A second pattern 607 represents extensive loss across the entire inferior region. A third pattern 608 represents loss near the center of the inferior region, weighted slightly toward the temporal side.

A third set of patterns 609-613 represent diffuse patterns of loss of visual acuity, each with an island of relatively low loss. In a first pattern 609, the island of relatively low loss is in the center of the temporal side, and a second pattern 610 has the island of relatively low loss covering the inferior/temporal quadrant. A third pattern 611 has the relatively low loss window near the center of the temporal side, extending toward the center of the visual field, and a fourth pattern 612 has a small low loss window in the inferior/temporal quadrant. A fifth pattern 613 has the relatively low loss window at the bottom of the visual field near the center of the inferior region. A fourth set of patterns 614-617 includes a first pattern 614 representing an intact field and a second pattern 615 representing loss across the entire field. A third pattern 616 represents loss in the temporal region of the visual field, and a fourth pattern 617 representing loss in the nasal region of the visual field.

Figure 7:
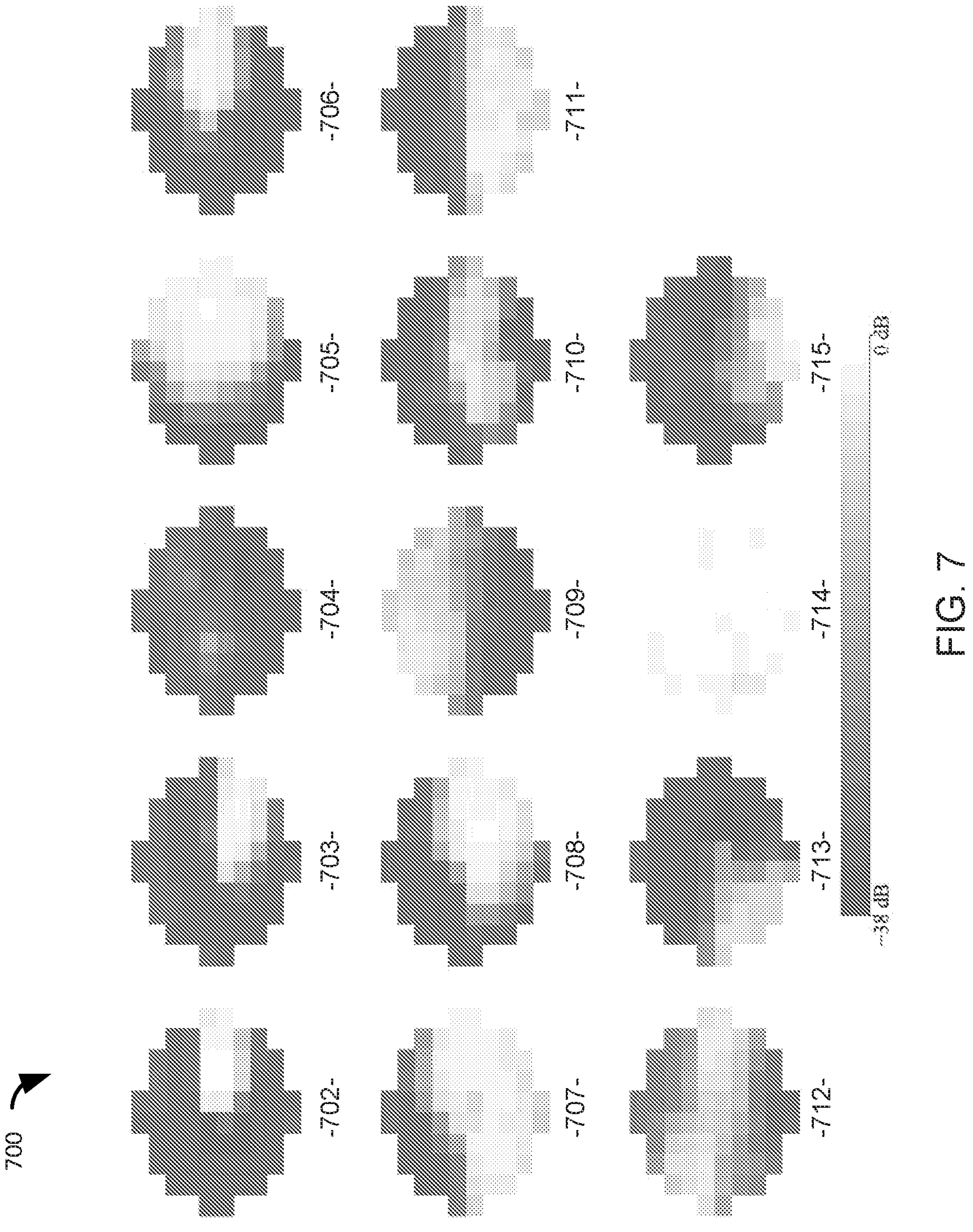
FIG. 7 illustrates an example of an archetypal basis set of visual field patterns that can be used at the pattern decomposition component for patients with end-stage glaucoma.

FIG. 7 illustrates an example of an archetypal basis set 700 of visual field patterns that can be used at the pattern decomposition component 324 for patients with end-stage glaucoma. The archetypal patterns 702-715 can be divided into five general categories. A first set of patterns 702, 703, and 706 represent temporal sparing. A second set of patterns 709 and 711 represent hemifield loss of visual acuity. A third set of patterns 710 and 712 represent diffuse patterns of loss of visual acuity, each with an island of relatively low loss. A fourth set of patterns 705, 707, and 708 represent loss of vision in the nasal region. A fifth set of patterns includes a first pattern 714 representing an intact field, a second pattern 713 representing inferonasal quadrant sparing, a third pattern 715 representing nearly total loss across the entire field, and a fourth pattern 704 representing total loss across the entire field.

The set of coefficients from the pattern decomposition component 324 can be provided to a feature extractor 326 to generate a feature vector representing the patient. In addition to the inclusion of one or more of the decomposition coefficients, the feature extractor can calculate a mean deviation value across all locations, a pattern standard deviation, and a mean absolute error for each patient representing the error between the measured visual field data and the model provided by the pattern decomposition. Specifically, the mean absolute error can be calculated as the mean absolute difference between total deviation values at each of the locations in the original 10-2 visual field exam and a reconstructed baseline visual field, which is the sum of the archetypal VF patterns weighted by the decomposition coefficients calculated for the patient. The feature vector can also include biometric parameters associated with the patient, including categorical predictors, such as predictors representing biological sex, medical history, and the presence or absence of various medical conditions, as well as integral or ratio parameters, such as age, blood glucose level, blood pressure, intraocular pressure, or similar parameters. Where multiple sets of visual field data are acquired for a patient over time, a change, measure of central tendency, or measure of deviation for any of these values can also be used in the feature vector.

The machine learning model 302 can utilize one or more pattern recognition algorithms, implemented, for example, as classification and regression models, each of which analyze the extracted feature vector to assign a clinical parameter to the user. It will be appreciated that the clinical parameter can be categorical or continuous. For example, a categorical parameter can represent a selected intervention, a degree of expected or actual glaucoma progression, a degree of expected change in visual acuity over a defined time frame, an range of expected times for a defined degree of change in visual acuity, or a range of binned likelihood values for any of these categories. A continuous parameter can represent an expected change in a metric of visual acuity (e.g., mean deviation values for a visual field test), an expected rate of change in a metric of visual acuity, a predicted time for a defined change in visual acuity to occur, or a likelihood that a given patient falls within one of the categories.

Where multiple classification and regression models are used, the machine learning model 302 can include an arbitration element can be utilized to provide a coherent result from the various algorithms. Depending on the outputs of the various models, the arbitration element can simply select a class from a model having a highest confidence, select a plurality of classes from all models meeting a threshold confidence, select a class via a voting process among the models, or assign a numerical parameter based on the outputs of the multiple models. Alternatively, the arbitration element can itself be implemented as a classification model that receives the outputs of the other models as features and generates one or more output classes for the patient.

The machine learning model 302, as well as any constituent models, can be trained on training data representing the various classes of interest. The training process of the machine learning model 302 will vary with its implementation, but training generally involves a statistical aggregation of training data into one or more parameters associated with the output classes. Any of a variety of techniques can be utilized for the models, including support vector machines, regression models, self-organized maps, fuzzy logic systems, data fusion processes, boosting and bagging methods, rule-based systems, or artificial neural networks.

For example, an SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. An SVM classifier utilizes a user-specified kernel function to organize training data within a defined feature space. In the most basic implementation, the kernel function can be a radial basis function, although the systems and methods described herein can utilize any of several linear or non-linear kernel functions.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

A regression model applies a set of weights to various functions of the extracted features, most commonly linear functions, to provide a continuous result. In general, regression features can be categorical, represented, for example, as zero or one, or continuous. In a logistic regression, the output of the model represents the log odds that the source of the extracted features is a member of a given class. In a binary classification task, these log odds can be used directly as a confidence value for class membership or converted via the logistic function to a probability of class membership given the extracted features.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used, but a continuous parameter can be computed according to a number of decision trees that select a given task. Regardless of the specific model employed, the clinical parameter generated at the machine learning model 302 can be provided to a user at the display 318 via a user interface 326 or stored on the non-transitory computer readable medium 320, for example, in an electronic medical record associated with the patient.

Figure 8:
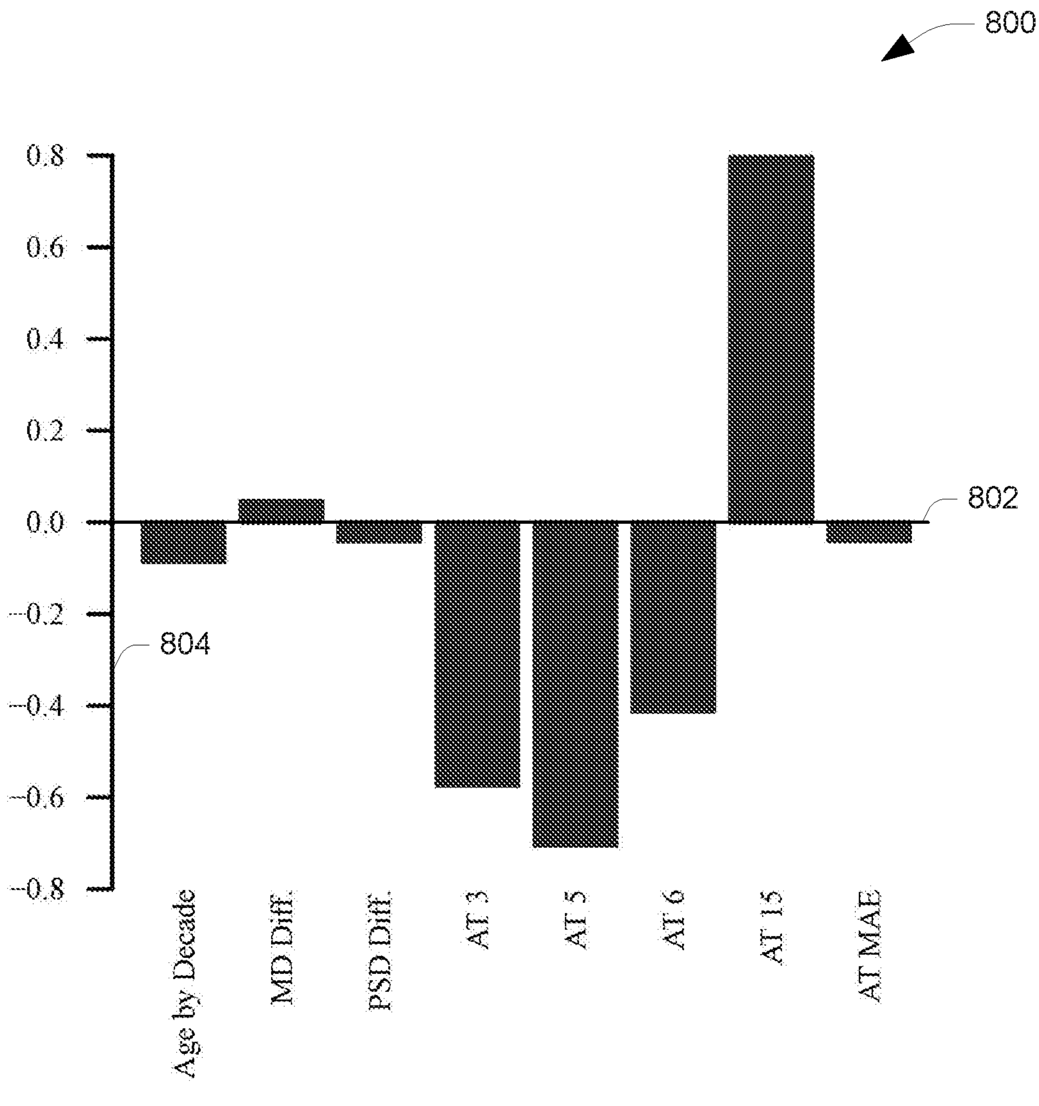
FIG. 8 is a bar chart illustrating the results of a regression model showing the relationship between various regression predictors, corresponding to the features used in the system of FIG. 3, to a rate of change in visual acuity, specifically the mean deviation value, for all patients.

FIG. 8 is a bar chart 800 illustrating the results of a regression model showing the relationship between various regression predictors, corresponding to the features used in the system of FIG. 3, to a rate of change in visual acuity, specifically the mean deviation value, for all patients. The features representing decomposition coefficients correspond to a selection of the visual field patterns shown in FIG. 2. A horizontal axis 802 represents the coefficient assigned to each of the plurality of features in the regression, represented as bars on the horizontal axis 804. It will be appreciated that the mean deviation is a negative value, and thus the coefficients representing a worsening of visual acuity in the chart are negative coefficients. As can be seen from the chart, the best predictors for rapid loss of visual acuity are high decomposition coefficient values for patterns AT 3, representing loss in the periphery of the nasal side of the superior region of the visual field, AT 5, representing loss in the periphery of the nasal side of the inferior region of the visual field, and AT 6, representing more widespread loss of visual acuity on the nasal side of the inferior region of the visual field.

Figure 9:
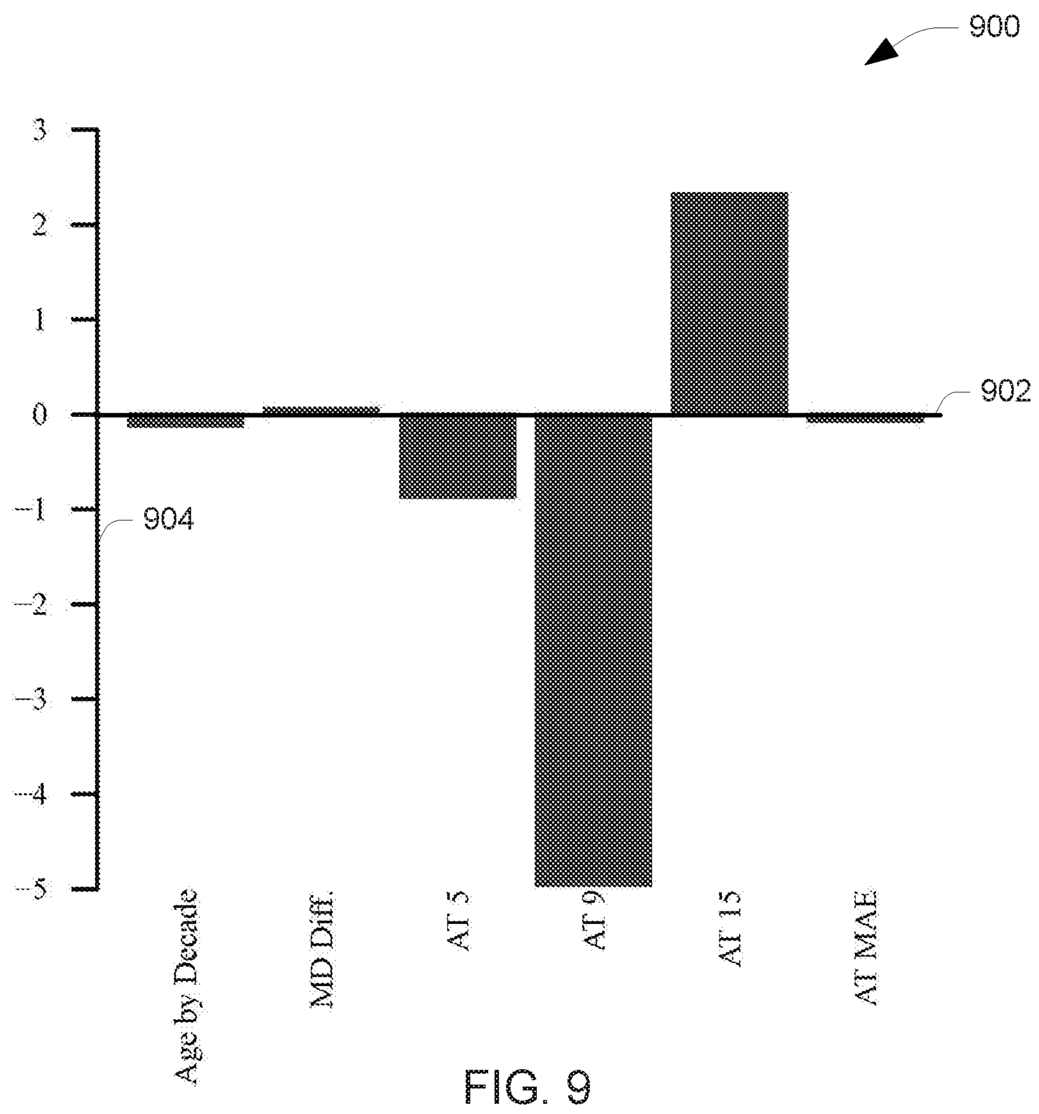
FIG. 9 is a bar chart illustrating the results of a regression model showing the relationship between various regression predictors, corresponding to the features used in the system of FIG. 3, to a rate of change in visual acuity, specifically the mean deviation value for all patients.

FIG. 9 is a bar chart 900 illustrating the results of a regression model showing the relationship between various regression predictors, corresponding to the features used in the system of FIG. 3, to a rate of change in visual acuity, specifically the mean deviation value, for patients with mild or moderate glaucoma. The features representing decomposition coefficients correspond to the visual field patterns shown in FIG. 2. A horizontal axis 902 represents the coefficient assigned to each of the plurality of features in the regression, represented as bars on the horizontal axis 904. As can be seen from the chart, by far the best predictor for rapid loss of visual acuity is a high decomposition coefficient values for pattern AT 9, representing diffuse loss through most of the visual field with an island of relatively low loss in the center of the temporal region of the visual field. Pattern AT 5, representing loss in the periphery of the nasal side of the inferior region of the visual field, remains a significant predictor for rapid progression of the disease even when patients with severe glaucoma are removed from the regression analysis.

For end-stage glaucoma, certain archetypes from FIG. 7 are associated with different progressions of the disease when they are the primary, or highest weight, pattern in the linear decomposition. These different expected progressions of disease are referred to herein as subtypes of glaucoma, and subtypes can be defined based on progressions from mild, moderate, severe, or end-stage glaucoma. For example, patients for which the primary pattern is the nasal loss pattern labeled 705, it is likely that the patient will proceed toward total loss, whereas when the primary pattern is the nasal loss pattern labelled 708, progression toward total loss is significantly more likely. The inventors have identified a number of these subtypes, and the machine learning model 302 can be trained to distinguish among these subtypes based on visual field data.

Figure 10:
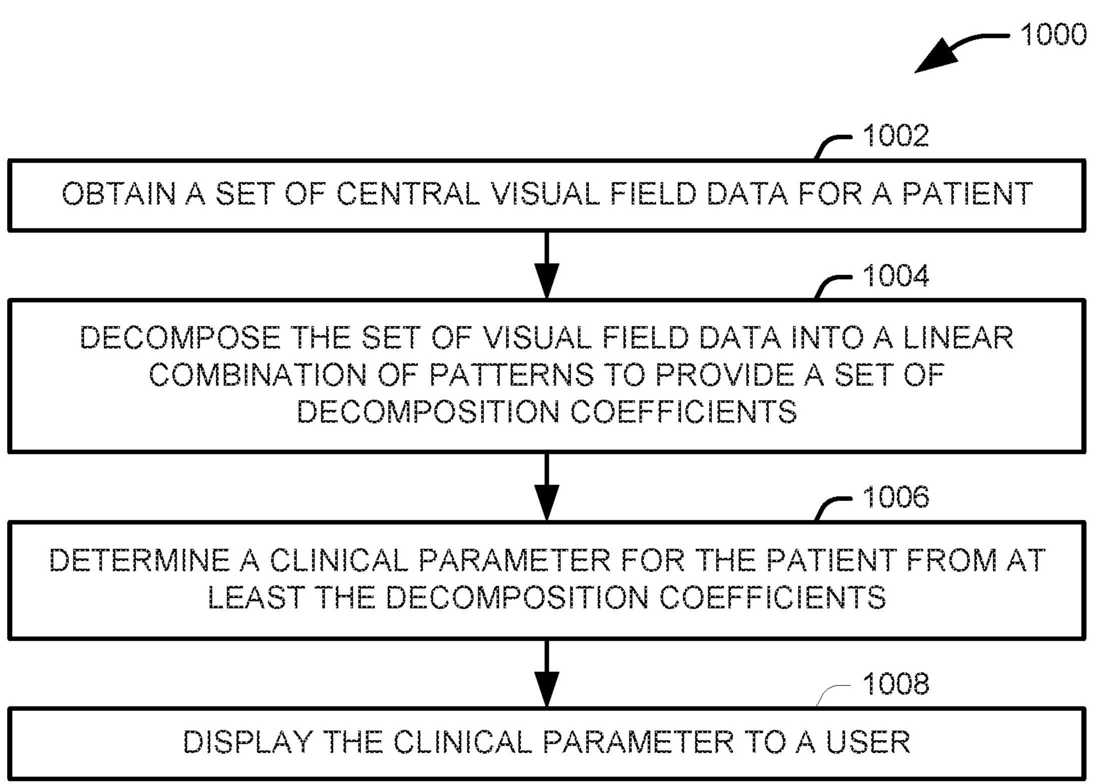
FIG. 10 illustrates one example of a method for predicting clinical parameters relating to glaucoma from central visual field patterns.

In view of the foregoing structural and functional features described above, methods in accordance with various aspects of the present invention will be better appreciated with reference to FIG. 10. While, for purposes of simplicity of explanation, the method of FIG. 10 is shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a method in accordance with an aspect the present invention.

FIG. 10 illustrates one example of a method 1000 for predicting clinical parameters relating to glaucoma from central visual field patterns. At 1002, a set of visual field data is obtained for a patient representing, for each of a plurality of locations in the central region of the eye, a deviation in sensitivity to a visual stimulus from an age-adjusted normal value. For example, the set of visual field data can be acquired as part of a 10-2 visual field test. At 1004, the set of visual field data into a linear combination of patterns defined via archetypal analysis over a corpus of visual field data to provide a set of decomposition coefficients. Examples of patterns providing appropriate basis sets can be found in FIGS. 2 and 4-6, although it will be appreciated that other basis sets can be used, depending on the cohort to which the patient belongs. At 1006, at least one clinical parameter for the patient at a machine learning model from at least the set of decomposition coefficients. For example, the clinical parameter can represent a rate of progression of glaucoma or a likelihood that a particular intervention will be successful for a given model, with the machine learning model trained on a corpus of labeled training data to provide the clinical parameter for novel examples. At 1008, the determined at least one clinical parameter is provided to a user at a display.

Figure 11:
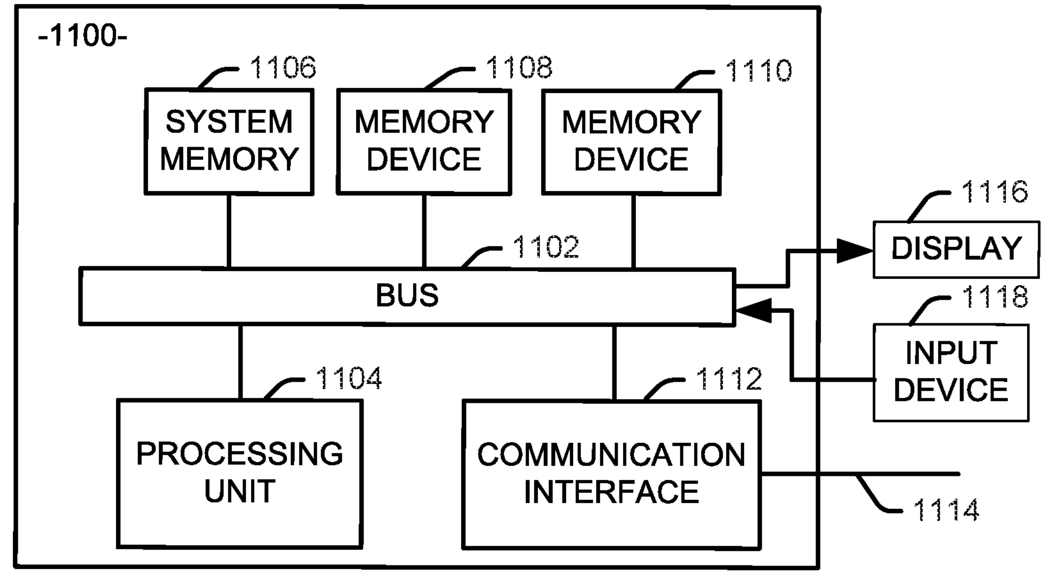
FIG. 11 is a schematic block diagram illustrating an exemplary system of hardware components capable of implementing examples of the systems and methods disclosed herein.

FIG. 11 is a schematic block diagram illustrating an exemplary system 1100 of hardware components capable of implementing examples of the systems and methods disclosed in FIGS. 1-10. The system 1100 can include various systems and subsystems. The system 1100 can be a personal computer, a laptop computer, a workstation, a computer system, an appliance, an application-specific integrated circuit (ASIC), a server, a server blade center, a server farm, etc.

The system 1100 can includes a system bus 1102, a processing unit 1104, a system memory 1106, memory devices 1108 and 1110, a communication interface 1112

(e.g., a network interface), a communication link 1114, a display 1116 (e.g., a video screen), and an input device 1118 (e.g., a keyboard and/or a mouse). The system bus 1102 can be in communication with the processing unit 1104 and the system memory 1106. The additional memory devices 1108 and 1110, such as a hard disk drive, server, stand-alone database, or other non-volatile memory, can also be in communication with the system bus 1102. The system bus 1102 interconnects the processing unit 1104, the memory devices 1106-1110, the communication interface 1112, the display 1116, and the input device 1118. In some examples, the system bus 1102 also interconnects an additional port (not shown), such as a universal serial bus (USB) port.

The processing unit 1104 can be a computing device and can include an application-specific integrated circuit (ASIC). The processing unit 1104 executes a set of instructions to implement the operations of examples disclosed herein. The processing unit can include a processing core. The additional memory devices 1106, 1108, and 1110 can store data, programs, instructions, database queries in text or compiled form, and any other information that can be needed to operate a computer. The memories 1106, 1108, and 1110 can be implemented as computer-readable media (integrated or removable) such as a memory card, disk drive, compact disk (CD), or server accessible over a network. In certain examples, the memories 1106, 1108, and 1110 can comprise text, images, video, and/or audio, portions of which can be available in formats comprehensible to human beings. Additionally or alternatively, the system 1100 can access an external data source or query source through the communication interface 1112, which can communicate with the system bus 1102 and the communication link 1114.

In operation, the system 1100 can be used to implement one or more parts of a diagnostic imaging system in accordance with the present invention. Computer executable logic for implementing the diagnostic imaging system resides on one or more of the system memory 1106, and the memory devices 1108, 1110 in accordance with certain examples. The processing unit 1104 executes one or more computer executable instructions originating from the system memory 1106 and the memory devices 1108 and 1110. The term "computer readable medium" as used herein refers to a medium that participates in providing instructions to the processing unit 1104 for execution.

Specific details are given in the above description to provide a thorough understanding of the embodiments. However, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps, and means described above can be done in various ways. For example, these techniques, blocks, steps, and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine-readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes but is not limited to portable or fixed storage devices, optical storage devices, wireless channels, and/or various other storage mediums capable of storing that contain or carry instruction(s) and/or data.

In the preceding description, specific details have been set forth in order to provide a thorough understanding of example implementations of the invention described in the disclosure. However, it will be apparent that various implementations may be practiced without these specific details. For example, circuits, systems, networks, processes, and other components may be shown as components in block diagram form in order not to obscure the example implementations in unnecessary detail. In other instances, well-known circuits, processes, algorithms, structures, and techniques may be shown without unnecessary detail in order to avoid obscuring the examples. The description of the example implementations will provide those skilled in the art with an enabling description for implementing an example of the invention, but it should be understood that various changes may be made in the function and arrangement of elements without departing from the spirit and scope of the invention. Accordingly, the present invention is intended to embrace all such alterations, modifications, and variations that fall within the scope of the appended claims.

Having described the invention, we claim:

1. A system comprising:

a processor;

an output device; and a non-transitory computer readable medium storing instructions executable by the processor to provide:

a pattern decomposition component that receives a set of visual field data for a patient representing, for each of a plurality of locations in the central region of an eye of the patient, a deviation in sensitivity to a visual stimulus from an age-adjusted normal value and decomposes the set of visual field data into a linear combination of a set of patterns defined via archetypal analysis over a corpus of visual field data to provide a set of decomposition coefficients;

a machine learning model that determines a clinical parameter for the patient from at least the set of decomposition coefficients; and a user interface that provides the determined clinical parameter to a user at the output device.

2. The system of claim 1, further comprising a preclassifier that classifies the patient into one of a plurality of categories based on at least one metric associated with the eye and selects the set of patterns from a plurality of sets of patterns defined via archetypal analysis according to the category into which the patient is classified.

3. The system of claim 1, wherein the set of patterns defined via archetypal analysis represents patterns seen in end-stage glaucoma and comprises a first subset of patterns representing temporal-sparing, a second subset of patterns representing hemifield loss, a third subset of patterns representing a central island of intact vision, a fourth subset of patterns representing nasal loss, and patterns representing nearly total loss, total loss, inferonasal quadrant sparing, and nearly intact central vision.

4. The system of claim 1, wherein the set of patterns defined via archetypal analysis represents patterns seen in severe glaucoma and comprises a first subset of patterns representing loss of visual acuity in the superior portion of the visual field, a second subset of patterns representing loss of visual acuity in the inferior portion of the visual field, a third subset of patterns representing diffuse patterns of loss of visual acuity, each with an island of relatively low loss, and patterns representing an intact visual field, loss across the entire field, loss in the temporal region of the visual field, and loss in the nasal region of the visual field.

5. The system of claim 1, wherein the set of patterns defined via archetypal analysis represents patterns seen in one of mild glaucoma and moderate glaucoma and comprises a first subset of patterns representing loss of visual acuity in the superior portion of the visual field, a second subset of patterns representing loss of visual acuity in the inferior portion of the visual field, a third subset of patterns representing patterns of loss of visual acuity that are present in the superior and the inferior regions.

6. The system of claim 1, wherein the clinical parameter represents an expected rate of change in a measure of visual acuity for the eye.

7. The system of claim 1, wherein the machine learning model determines the clinical parameter from the set of decomposition coefficients and an additional feature representing the patient.

8. The system of claim 7, wherein the additional feature representing the patient is one of a mean deviation from the set of visual field data, a pattern standard deviation from the set of visual field data, and an intraocular pressure of the eye.

9. The system of claim 7, wherein the additional feature representing the patient is one of a blood pressure, blood glucose level, age, and sex of the patient.

10. The system of claim 7, wherein the additional feature representing the patient is mean absolute difference between total deviation values at each of the plurality of locations in visual field pattern and a reconstructed baseline visual field generated as the sum of the set of patterns defined via archetypal analysis weighed by the set of coefficients.

11. A system comprising:

a processor;

an output device; and a non-transitory computer readable medium storing instructions executable by the processor to provide:

a preclassifier that classifies the patient into one of a plurality of categories representing the severity of glaucoma for the patient and selects the set of patterns from a plurality of sets of patterns defined via archetypal analysis according to the category into which the patient is classified;

a pattern decomposition component that receives a set of visual field data for a patient representing, for each of a plurality of locations in the central region of an eye of the patient eye, a deviation in sensitivity to a visual stimulus from an age-adjusted normal value and decomposes the set of visual field data into a linear combination of the selected set of patterns defined via archetypal analysis to provide a set of decomposition coefficients;

a machine learning model that determines a clinical parameter for the patient from at least the set of decomposition coefficients; and a user interface that provides the determined clinical parameter to a user at the output device.

12. The system of claim 11, wherein determining the at least one clinical parameter for the patient at the machine learning model comprises determining the at least one clinical parameter at the machine learning model from the set of decomposition coefficients and an additional feature representing the patient selected as one of mean deviation from the set of visual field data, a pattern standard deviation from the set of visual field data, an intraocular pressure of the eye, a blood pressure of the patient, blood glucose level of the patient, an age of the patient, a sex of the patient, and a mean absolute difference between total deviation values at each of the plurality of locations in visual field pattern and a reconstructed baseline visual field generated as the sum of the set of patterns defined via archetypal analysis weighed by the set of coefficients.

13. The system of claim 11, wherein the plurality of sets of patterns comprises:

a first set of patterns defined via archetypal analysis, representing patterns seen in end-stage glaucoma and comprising a first subset of patterns representing temporal-sparing, a second subset of patterns representing hemifield loss, a third subset of patterns representing a central island of intact vision, a fourth subset of patterns representing nasal loss, and patterns representing nearly total loss, total loss, inferonasal quadrant sparing, and nearly intact central vision;

a second set of patterns defined via archetypal analysis represents patterns seen in severe glaucoma and comprises a first set of patterns representing loss of visual acuity in the superior portion of the visual field, a second set of patterns representing loss of visual acuity in the inferior portion of the visual field, a third set of patterns representing diffuse patterns of loss of visual acuity, each with an island of relatively low loss, and patterns representing an intact visual field, loss across the entire field, loss in the temporal region of the visual field, and loss in the nasal region of the visual field; and a third set of patterns defined via archetypal analysis represents patterns seen in one of mild glaucoma and moderate glaucoma and comprises a first set of patterns representing loss of visual acuity in the superior portion of the visual field, a second set of patterns representing loss of visual acuity in the inferior portion of the visual field, a third set of patterns representing patterns of loss of visual acuity that are present in the superior and the inferior regions.

14. The system of claim 11, wherein the preclassifier receives the set of visual field data, determines a mean deviation across the plurality of locations, and classifies the patient according to the determined mean deviation.

15. The system of claim 11, wherein the set of visual field data is a first set of visual field data and the preclassifier receives a second set of visual field data representing the entire eye and classifies the patient according to a metric determined from the second set of visual field data.

* * * * *